United States Patent [19]

Kuć et al.

[11] Patent Number: 5,001,155
[45] Date of Patent: Mar. 19, 1991

[54] β-IONONE DERIVATIVE AS ANTIFUNGAL AGENT

[75] Inventors: Joseph Kuć, Lexington, Ky.; Steven D. Salt, Kenosha, Wis.

[73] Assignee: University of Kentucky Research Foundation, Lexington, Ky.

[21] Appl. No.: 300,161

[22] Filed: Jan. 23, 1989

Related U.S. Application Data

[63] Continuation of Ser. No. 92,780, Sep. 3, 1987, abandoned.

[51] Int. Cl.⁵ .................. A01G 37/02; A61K 31/12
[52] U.S. Cl. ........................ 514/546; 560/187; 560/259
[58] Field of Search .............. 560/259, 187; 514/546

[56] References Cited

U.S. PATENT DOCUMENTS

| | | | |
|---|---|---|---|
| 3,928,645 | 12/1975 | Mookherjee et al. | 426/538 |
| 4,014,351 | 3/1977 | Pittet et al. | 131/17 |
| 4,363,331 | 12/1982 | Kaiser et al. | 131/275 |
| 4,474,816 | 10/1984 | Wilson, Jr. et al. | |

FOREIGN PATENT DOCUMENTS

| | | | |
|---|---|---|---|
| 746011 | 11/1966 | Canada | 560/259 |
| 57734 | 5/1981 | Japan | 560/259 |

OTHER PUBLICATIONS

Quieson: An inhibitor of the Germination of Peronospora Tabacina Conidia, Leppik et al., Phytochemistry, 1972, vol. 11, pp. 2055–2063.

Synthesis of dl-3-Isobutyroxy-β-ionone and dl-Dehydrovomifoliol, Mori, Agr. Biol. Chem, 37 (12), 2899–2905, 1973.

Mori, Kenji, Chem. Abstracts, vol. 80:83317j, 1974.

Leppik et al., Chem. Abstracts, 77:45659c, 1972.

*Primary Examiner*—Werren B. Lone
*Attorney, Agent, or Firm*—King & Schickli

[57] ABSTRACT

Novel 3-acyloxy-β-ionone derivatives of the formula I

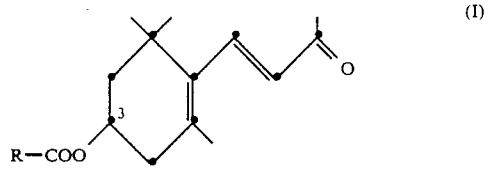

wherein R represents n-propyl, $C_4$–$C_5$-alkyl or $C_1$–$C_4$alkoxymethyl display very effective microbicidal activity. They can especially be used in form of microbicidal compositions to control plant-pathogenic microorganisms, preferably fungi of the order Oomycetes.

8 Claims, No Drawings

β-IONONE DERIVATIVE AS ANTIFUNGAL AGENT

This is a continuation of application Ser. No. 092,780, filed Sept. 3, 1987, abandoned.

BACKGROUND OF THE INVENTION

The present invention relates to novel esters of 3-hydroxy-β-ionone of formula I and its use to control fungal infections. Furthermore, the invention also relates to the preparation of these compounds and to compositions which contain at least one of these compounds as active ingredient.

SUMMARY OF THE INVENTION

In the formula I

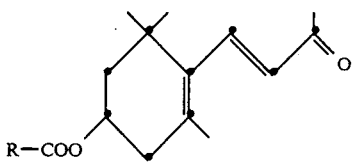

(I)

R represents n-propyl, $C_4$–$C_5$alkyl or $C_1$–$C_4$alkoxymethyl. Depending on the number of carbon atoms alkyl comprises butyl, isobutyl, sec.butyl, tert.butyl, pentyl, sec.pentyl, 1.1-dimethylpropyl, 2-methylbutyl, 2.2-dimethylpropyl, isopentyl (=3-methylbutyl) and 1-ethylpropyl. Accordingly, $C_1$–$C_4$alkoxy comprises methoxy, ethoxy, n-propoxy, isopropoxy, butoxy, isobutoxy, sec.butoxy and tert.butoxy.

Specific mention should be made of compounds wherein R is unbranched propyl, butyl and pentyl with n-propyl being preferred. Also preferred are compounds wherein R means methoxymethyl or ethoxymethyl The compounds of formula I are mainly oils which are stable at room temperature and have very valuable microbicidal properties. They can be used in agriculture or related fields preventively and curatively for controlling phytopathogenic microorganisms. The compounds of formula I are very well tolerated by cultivated plants.

The activities of compounds of formula I are directed preferably to plant diseases caused by Oomycetes and among them especially to Peronosporales. One of the targets is *Peronospora tabacina*, a pathogen of tobacco causing blue mold. Blue mold is a major disease of tobacco worldwide.

In Phytbchemistry 1972, vol. 11, pp. 2055–2063 it has been reported that tobacco plants are capable of producing 3-iso-butyroxy-β-ionone, an inhibitor of the germination of *P. tabacina* conidia. The natural product 3-isobutyroxy-β-ionone has been named "Quiesone".

DETAILED DESCRIPTION OF THE INVENTION

It has been found that the 3-alkanoyl-β-ionone derivatives of the formula I display much broader activities against Peronosporales and other plantpathogenic microorganisms than does Quiesone.

The carboxyl group of the β-ionone derivatives of the formula I is linked to an asymmetric carbon atom in the ring. Provided that there is no additional asymmetric centre in the acyl moiety, the compounds will be obtained in the form of two enantiomers. Depending on the synthesis method, a mixture of both enantiomers or one single enantiomer can be prepared. Racemic 3(+)-hydroxy-β-ionone can be resolved by standard methods, e.g. by acylation with an optical active acid derivative. After separation and cleavage of the resulting diastereomeric mixture, pure (R)- or (S)-3-hydroxy-β-ionone can be obtained.

Examples of useful optical active acid derivatives as chiral auxiliaries are e.g. camphanic acid (Helv. 51, 1587, (1968); camphorsulfonic acid (Tetrahedron Lett. 1969, 313); 3-β-acetoxy-Δ⁵-etienic acid (Tetrahedron 5, 70 (1959); J. Org. Chem. 33, 4242) or α-methoxy-α-trifluoromethylphenyl acetic acid (J. Am. Chem. Soc. 1973, 95, 239).

Optical pure 3(S)-acyloxy-β-ionone can also be prepared from 3(R)-hydroxy-β-ionone and the corresponding carboxylic acid by using diethyl azodicarboxylate/triphenylphosphine (Tetrahedron Lett. 1973, 1619 or Synthetic Comm. 16, 611 [1986].

The enantiomers have different biological properties.

The present invention relates to all pure isomers of formula I as well as mixtures thereof.

Another aspect of the invention are microbicidal compositions containing, as at least one active ingredient, a compound of the formula I, as well as the use of such compositions for controlling phytopathogenic microorganisms, especially harmful fungi, and for the preventive treatment of plants to protect them from attack by such microorganisms.

Still another aspect of the invention is a method of treating plants or parts of plants or the locus, which comprises applying thereto the compounds of formula I or the novel compositions.

Target crops to be protected within the scope of the present invention comprise e.g. the following species of plants: cereals (wheat, barley, rye, oats, rice, sorghum and related crops), beet (sugar beet and fodder beet), drupes, pomes and soft fruit (apples, pears, plums, peaches, almonds, cherries, strawberries, raspberries and blackberries), leguminous plants (beans, lentils, peas, soybeans), oil plants (rape, mustard, poppy, olives, sunflowers, coconuts, castor oil plants, cocoa beans, groundnuts), cucumber plants (cucumber, marrows, melons) fibre plants (cotton, flax, hemp, jute), citrus fruit (oranges, lemons, grapefruit, mandarins), vegetables (spinach, lettuce, asparagus, cabbages, carrots, onions, tomatoes, potatoes, paprika), lauraceae (avocados, cinnamon, camphor), or plants such as maize, tobacco, nuts, coffee, sugar cane, tea, vines, hops, bananas and natural rubber plants, as well as ornamentals (composites), areas of grass, embankments or general low cover crops which counteract erosion or desiccation of the soil and are useful in cultures of trees and perennials (fruit plantations, hop plantations, maize fields, vineyards, etc.).

The compounds of formula I are normally applied in the form of compositions and can be applied to the crop area or plant or substrate to be treated, simultaneously or in succession, with further compounds. These compounds can be both fertilizers or micronutrient donors or other preparations that influence plant growth. They can also be selective herbicides, fungicides, bactericides, nematicides, molluscides or mixtures of several of these preparations, if desired together with further carriers, surfactants or application promoting adjuvants customarily employed in the art of formulation. Suitable carriers and adjuvants can be solid or liquid and correspond to the substances ordinarily employed in formulation technology, e.g. natural or regenerated mineral substances, solvents, dispersants, wetting agents, tackifiers, binders or fertilizers. Phospholipids are also useful formulation assistants.

A preferred method of applying a compound of the formula I, or an agrochemical composition which contains at least one of said compounds, is foliar application. The number of applications and the rate of application depend on the risk of infestation by the corresponding pathogen (type of fungus). However, the compounds of formula I can also penetrate the plant through the roots via the soil (systemic action) by impregnating the locus of the plant with a liquid composition, or by applying the compounds in solid form to the soil, e.g. in granular form (soil application). The compounds of formula I may also be applied to seeds (coating) by impregnating the seeds either with a liquid formulation containing a compound of the formula I, or coating them with a solid formulation. In special cases, further types of application are also possible, e.g. selective treatment of the plant stems or buds.

The compounds of formula I are used in unmodified form or, preferably, together with the adjuvants conventionally employed in the art of formulation, and are therefore formulated in known manner to emulsifiable concentrates, coatable pastes, directly sprayable or dilutable solutions, dilute emulsions, wettable powders, soluble powders, dusts, granulates, and also encapsulations in e.g. polymer substances. As with the nature of the compositions, the methods of application, such as spraying, atomizing, dusting, scattering or pouring, are chosen in accordance with the intended objectives and the prevailing circumstances. Advantageous rates of application are normally from 50 g to 5 kg of active ingredient (a.i.) per hectare, preferably from 100 g to 2 kg a.i./ha, most preferably from 200 g to 600 g a.i./ha.

The formulations, i.e. the compositions or preparations containing the compound (active ingredient) of formula I and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

The compositions may also contain further ingredients such as stabilizers, antifoams, viscosity regulators, binders, tackifiers as well as fertilizers or other active ingredients in order to obtain special effects.

The surfactant customarily employed in the art of formulation are described e.g. in "McCutcheon's Detergents and Emulsifiers Annual", MC Publishing Corp. Ringwood, N.J., 1981.

The agrochemical compositions usually contain 0.1 to 99%, preferably 0.1 to 95%, of a compound of formula I, 99.9 to 1%, preferably 99.8 to 5%, of a solid or liquid adjuvant, and 0 to 25%, preferably 0.1 to 25%, of a surfactant.

Whereas commercial products are preferably formulated as concentrates, the end user will normally employ dilute formulations.

The compounds of formula I are obtained by conventional esterification of either racemic or enantiomeric pure 3(R)- or 3(S)-hydroxy-β-ionone (formula II, IIa, IIb)

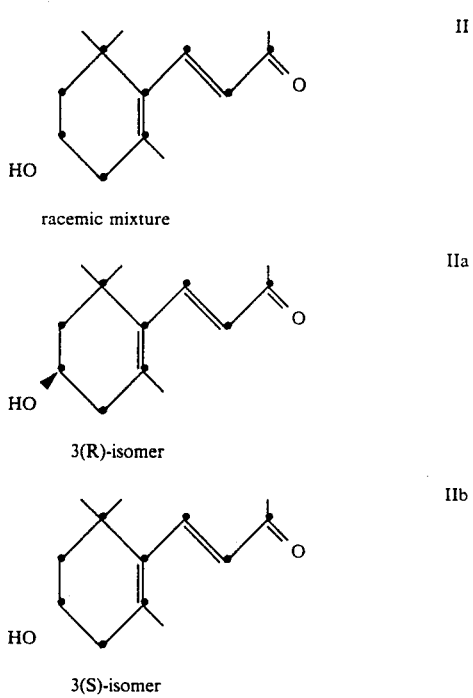

The starting material of formulae II and IIa are generally known compounds and can be prepared by known procedures.

The synthesis of the racemic compound II and the corresponding acetate (3-acetoxy- -ionone) are described in J. Chem. Soc. (C) 1971, 406 and in Bull. Soc.-Jp. 1982, 1907.

Examples of an enantioselective synthesis of IIa or of the corresponding acetyl-derivative are also described, such as for example in Pure Appl. Chem. 51, 535 (1979), Helv. 63, 1412 (1980), Tetrahedron 30, 1065 (1974).

Esterification (II→I) can be accomplished by treating 3-hydroxy-β-ionone II, IIa or IIb with a carboxylic acid RCOOH in the presence of an inorganic acid or with activators such as dicyclohexylcarbodiimide or diethyl azodicarboxylate/triphenylphosphine (Synthesis 1979, 561, ibid. 1981, 1).

Esterification can also effected by treating either the alcohol II, IIa or IIb with a carboxylic acid halide or an anhydride in the presence of a base, such as common tert. amine (e.g. triethylamine or pyridine) and, if desired, with a catalytical amount of 4-dimethylaminopyridine.

The reaction is preferably carried out in inert solvents such as hydrocarbons, ether or nitriles (e.g. acetonitril). Pyridine can also be used as solvent. The temperature may be in the range of from −10 to +80° C., preferably at room or slightly elevated temperature. As inorganic acids there may be used hydrochloric or hydrobromic acid, sulfuric acid, phosphoric acid, nitric acid and the like.

The esters of formula I may also be obtained by transesterification of a known 3-acyloxy β-ionone, such as 3-acetoxy-β-ionone, as shown hereunder.

The esters of formula I can, for example, be synthesized by hydrolysis of the known 3(R)-acetoxy-β-ionone and subsequent acylation by the use of the appropriate acid chlorides. Method: First, the acetoxy-β-ionone was saponified by dissolving the compound (10 mg/ml final concentration) in 10% w/v KOH in methanol. After incubation for 60 minutes at room temperature, the solution was diluted 10:1 v/v with ice water and extracted 2 times with 2.5 volumes (original predilution volume) of diethyl ether. The ether extracts were pooled, washed once with 10 mM pH 6.8 potassium phosphate buffer and twice with distilled deionized water and then dried at least overnight at 4° C. with solid anhydrous $Na_2SO_4$.

The dried ether solution was then evaporated to dryness under $N_2$ and the oily residue, largely (3R)-3-hydroxy-$\beta$-ionone, was weighed.

For reesterification, the above product was redissolved in dry pyridine (10 ml/25 mg) and cooled with ice. To each 10 ml of the pyridine solution was added 10 ml anhydrous diethyl ether containing 25 mg/ml of acid chloride (e.g. butyroyl chloride, methoxy acetyl chloride, valeroylbromide, etc.) with stirring. The mixture was agitated, sealed under $N_2$, and left 12 h at room temperature. A color varying from orange to intense cherry red, depending upon the acid chloride utilized, developed in each reaction mixture. The reaction was terminated by the addition of ice water (about 5-6 volumes) and the diluted mixture was extracted twice with diethyl ether (approximately twice the original reaction volume for each extraction). The ether extracts were combined, washed sequentially with water (twice), 5% (v/v) acetic acid, saturated aqueous $NaHCO_3$, and then 10% w/v aqueous NaCl (twice). Aqueous NaCl was found necessary in the final washes as the ether solution tended to form a stable emulsion when shaken with distilled water. The washed ether solution was then dried with solid anhydrous $Na_2SO_4$ at least 24 h at 4° C.

The ether solutions were taken to dryness under $N_2$ and the yellow to orange oily residue was then weighed. The compounds were stored in ethanol solution at $-20°$ C. in sealed Wheaton vials.

Purity of products was determined by gas chromatography.

Conventional methods of preparing $\beta$-ionone derivatives of the formula I starting from 3-hydroxy-$\beta$-ionone may be exemplified as follows:

PREPARATION EXAMPLE 1

Preparation of the Compound

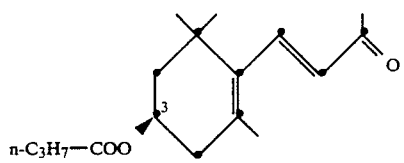

3(R)-butyroyloxy-$\beta$-ionone 5 ml of butyric anhydride are added to 4.15 g (0.0199 moles) of 3(R)-hydroxy-$\beta$-ionone dissolved in 50 ml of pyridine. The reaction mixture is stirred overnight and poured into 500 ml of ice water. The aqueous emulsion is extracted with two 400 ml portions of diethylether and the combined organic phases are washed with 400 ml of water, 400 ml of diluted sulfuric acid (5%) and 200 ml of saturated $NaHCO_3$-solution. The ether solution is then dried over $Na_2SO_4$ and evaporated, affording 6.3 g of a yellow oil which is purified through a column of 100 g of silica gel (eluant: hexan/tetrahydrofuran 5:1). Yield: 4.8 g of 3(R)-butyroyloxy-$\beta$-ionone as a pale yellow liquid, b.p. 115°-117° C./0.01 mbar; $(\alpha)_D 20 = -58.2 \pm 1°$ (C = 1.457%) in acetone).

PREPARATION EXAMPLE 2

Preparation of the Compound

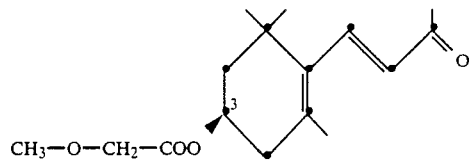

3(R)-methoxyacetoxy-$\beta$-ionone 1.1 ml of methoxyacetylchloride are added to a solution of 2.1 g (0.01 mol) of 3(R)-hydroxy-$\beta$-ionone in 25 ml of pyridine at 10° to 15° C. under cooling. After stirring overnight, the reaction mixture is poured into a mixture of 200 ml of ether/hexane (1:1). The aqueous phase is separated and the organic solution subsequently washed with water, ice-cooled aqueous sulfuric acid and finally with aqueous sodiumbicarbonate. After drying over $Na_2SO_4$, the solvent is stripped off and the oily residue is distilled to yield 2.4 g of 3(R)-methoxyacetoxy-$\beta$-ionone,, b.p. 105° C./0.01 mbar; $(\alpha)_D 20 = -53.4 \pm 0.6°$ (C = 1.658% in acetone).

The following compounds can be prepared in a manner similar to that of examples 1 and 2.

TABLE

| No. | R | Konfiguration at C-3 | physical data |
|---|---|---|---|
| 1a | $CH_3CH_2CH_2-$ | R | b.p. 115–117°/ 0.01 mbar |
| 1b | $CH_3CH_2CH_2-$ | S | |
| 1c | $CH_3CH_2CH_2-$ | rac. mixture | |
| 2a | $CH_3CH_2CH_2CH_2-$ | R | b.p. 115°/ 0.01 mbar |
| 2b | $CH_3CH_2CH_2CH_2-$ | S | |
| 2c | $CH_3CH_2CH_2CH_2-$ | rac. mixture | |
| 3a | $CH_3-CH-CH_2-$<br>$\quad\quad\;\;\mid$<br>$\quad\quad\;\;CH_3$ | R | $n_D^{20}$ 1.5000 |
| 3b | $CH_3-CH-CH_2-$<br>$\quad\quad\;\;\mid$<br>$\quad\quad\;\;CH_3$ | S | |
| 3c | $CH_3-CH-CH_2-$<br>$\quad\quad\;\;\mid$<br>$\quad\quad\;\;CH_3$ | rac. mixture | |
| 4a | $CH_3-CH_2-CH-$<br>$\quad\quad\quad\quad\;\;\mid$<br>$\quad\quad\quad\quad\;\;CH_3$ | R | |
| 4b | $CH_3-CH_2-CH-$<br>$\quad\quad\quad\quad\;\;\mid$<br>$\quad\quad\quad\quad\;\;CH_3$ | S | |
| 4c | $CH_3-CH_2-CH-$<br>$\quad\quad\quad\quad\;\;\mid$<br>$\quad\quad\quad\quad\;\;CH_3$ | rac. mixture | |
| 5a | $\quad\;\;CH_3$<br>$CH_3-\!\!\!\!+\!\!\!\!-$<br>$\quad\;\;CH_3$ | R | $n_D^{20}$ 1.4918 |

TABLE-continued

| No. | R | Konfiguration at C-3 | physical data |
|---|---|---|---|
| 5b | CH$_3$—C(CH$_3$)—CH$_3$ | S | |
| 5c | CH$_3$—C(CH$_3$)—CH$_3$ | rac. mixture | |
| 6a | CH$_3$(CH$_2$)$_4$— | R | n$_D^{20}$ 1.4978 |
| 6b | CH$_3$(CH$_2$)$_4$— | S | |
| 6c | CH$_3$(CH$_2$)$_4$— | rac. mixture | |
| 7a | CH$_3$—O—CH$_2$— | R | b.p. 105°/0.01 mbar |
| 7b | CH$_3$—O—CH$_2$— | S | |
| 7c | CH$_3$—O—CH$_2$— | rac. mixture | |
| 8a | CH$_3$CH$_2$—O—CH$_2$— | R | b.p. 110°/0.01 mbar |

TABLE

| No. | R | Konfiguration at C-3 | physical data |
|---|---|---|---|
| 8b | CH$_3$CH$_2$—O—CH$_2$— | S | |
| 8c | CH$_3$CH$_2$—O—CH$_2$— | rac. mixture | |
| 9a | isoC$_3$H$_7$—O—CH$_2$— | R | oil |
| 9b | isoC$_3$H$_7$—O—CH$_2$— | S | |
| 9c | isoC$_3$H$_7$—O—CH$_2$— | rac. mixture | |

FORMULATION EXAMPLES

2. Formulation Examples for Liquid Active Ingredients of the Formula I (throughout, percentages are by weight)

| 2.1. Emulsifiable concentrates | (a) | (b) | (c) |
|---|---|---|---|
| a compound of Table 1 | 25% | 40% | 50% |
| calcium dodecylbenzenesulfonate | 5% | 8% | 6% |
| castor oil polyethylene glycol ether (36 moles of ethylene oxide) | 5% | — | — |
| tributylphenol polyethylene glycol ether (30 moles of ethylene oxide) | — | 12% | 4% |
| cyclohexanone | — | 15% | 20% |
| xylene mixture | 65% | 25% | 20% |

Emulsions of any required concentration can be produced from such

| 2.2. Solutions | (a) | (b) | (c) | (d) |
|---|---|---|---|---|
| a compound of Table 1 | 80% | 10% | 5% | 95% |
| ethylene glycol monomethyl ether | 20% | — | — | — |
| polyethylene glycol 400 (mol wt) | — | 70% | — | — |
| N-methyl-2-pyrrolidone | — | 20% | — | — |
| epoxidised coconut oil | — | — | 1% | 5% |
| petroleum distillate (boiling range 160–190° C.) | — | — | 94% | — |

These solutions are suitable for application in the form of microdrops.

| 2.3. Granulates | (a) | (b) |
|---|---|---|
| a compound of Table 1 | 5% | 10% |
| kaolin | 94% | — |
| highly dispersed silicic acid | 1% | — |
| attapulgite | — | 90% |

The active ingredient is dissolved in methylene chloride, the solution is sprayed onto the carrier, and the solvent is subsequently evaporated off in vacuo.

| 2.4. Dusts | (a) | (b) |
|---|---|---|
| a compound of Table 1 | 2% | 5% |
| highly dispersed silicic acid | 1% | 5% |
| talcum | 97% | — |
| kaolin | — | 90% |

Ready-for-use dusts are obtained by intimately mixing the carriers with the active ingredient.

| 2.5. Wettable powders | (a) | (b) | (c) |
|---|---|---|---|
| a compound of Table 1 | 25% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| octylphenol polyethylene glycol ether (7–8 moles of ethylene oxide) | — | 2% | — |
| highly dispersed silicic acid | 5% | 10% | 10% |
| kaolin | 62% | 27% | — |

The active ingredient is thoroughly mixed with the adjuvants and the mixture is thoroughly ground in a suitable mill, affording wettable powders which can be diluted with water to give suspensions of the desired concentration.

| 2.6. Emulsifiable concentrate | |
|---|---|
| a compound of Table 1 | 10% |
| octylphenol polyethlene glycol ether (4–5 moles of ethylene oxide) | 3% |
| calcium dodecylbenzenesulfonate | 3% |
| castor oil polyglycol ether (36 moles of ethylene oxide) | 4% |
| cyclohexanone | 30% |
| xylene mixture | 50% |

Emulsions of any required concentration can be obtained from this concentrate by dilution with water.

| 2.7. Dusts | (a) | (b) |
|---|---|---|
| a compound of Table 1 | 5% | 8% |
| talcum | 95% | — |
| kaolin | — | 92% |

Ready-for-use dusts are obtained by mixing the active ingredient with the carriers, and grinding the mixture in a suitable mill.

| 2.8. Extruder granulate | |
|---|---|
| a compound of Table 1 | 10% |
| sodium lignosulfonate | 2% |
| carboxymethylcellulose | 1% |
| kaolin | 87% |

The active ingredient is mixed and ground with the adjuvants, and the mixture is subsequently moistened with water. The mixture is extruded and then dried in a stream of air.

| 2.9. Coated granulate | |
|---|---|
| a compound of Table 1 | 3% |
| polyethylene glycol 200 (mol wt) | 3% |

| 2.9. Coated granulate | |
| --- | --- |
| kaolin | 94% |

The finely ground active ingredient is uniformly applied, in a mixer, to the kaolin moistened with polyethylene glycol. Non-dusty coated granulates are obtained in this manner.

| 2.10. Suspension concentrate | |
| --- | --- |
| a compound of Table 1 | 40% |
| ethylene glycol | 10% |
| nonylphenol polyethylene glycol (15 moles of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the adjuvants, giving a suspension concentrate from which suspensions of any desired concentration can be obtained by dilution with water.

3. Biological Examples 3.1. Inhibition of Sporangial Germination 3.11. Variant I Highly purified agar (Phytagar) was dissolved in deionized distilled water at a concentration of 1.2% w/v by heating in a microwave oven. The well-mixed solution was allowed to cool to 65° C., then poured into a standard glass petri dish forming a layer approximately 3 mm in thickness. After the agar was well-solidified, discs approximately 12 mm in diameter were cut from the agar layer using a #9 cork borer. Volume of each disc was approximately 0.42 ml. Discs were lifted with a spatula and placed on pre-cleaned, new 2.5×7.5 cm microscope slides, four discs per slide. The slides were then placed in glass petri dishes, one slide per dish, with Whatman #1 filter paper well-moistened with distilled water lining insides of both the bottom (under the slide) and top of the petri dishes. Into each disc 4.3 $\mu$l of absolute ethanol (control) or 4.3 $\mu$l of active compound dissolved in absolute ethanol was injected with a 10 $\mu$l Hamilton syringe. Preliminary experiments revealed this concentration (1% v/v, final) of ethanol to have negligible effect upon the germination of P. tabacina sporangia. After injection of compounds, the discs were allowed to stand at room temperature for at least 1 hour to permit full diffusion of injected material. Sporangia of P. tabacina (isolate Ky 79, freshly harvested from leaves of 3–4 leaf state Ky 14 burley tobacco plants) were washed on a 3 $\mu$ pore size paper and resuspended in cold distilled water to $2\times10^4$ sporangia/ml). After 1 hour, 10 $\mu$l of sporangia suspension was placed on the surface of each agar disc and distributed by gentle rubbing. This resulted in approximately 200 sporangia per agar disc examined. The filter paper liners of the petri dishes were then remoistened, if necessary, the lid securely settled on the lower dish, and the petri dishes containing the inoculated discs placed in the dark at 18° C.±1° C. for 18–20 hours. At this time, the petri dishes were opened, the slides dried by wiping with a paper tissue, and the discs on the slides examined at 100 × magnification with a microscope. At least 3 fields per disc (60–80 sporangia) were examined and total number and number germinated sporangia counted. Division of total number into number germinated gave absolute germination percentage. Division of absolute germination of controls (generally 60–80 percent absolute germination) into absolute percent germination of treatments gave percent germination of treatments relative to controls (100% relative germination) gave percent inhibition. $ED_{50}$ (concentration of compound required for 50% inhibition of germination relative to controls) was estimated by a semilog plot of percent relative germination arithmetic scale versus concentration of compounds tested (log scale).

All treatments were coded and at least two petri dishes (each containing four replicates per plate) of each treatment were included in each experiment. All highly active ($ED_{50}<0.01$ ppm) compounds were tested in at least three independent experiments.

3.12. Variant II

In another in vitro test, the substances ($10^2$–$10^{-8}$ ppm) were added to 1% water agar and poured into petri dishes. After cooling, the media were inoculated with 100 $\mu$l of a suspension of sporangia ($10^6$ s/ml) and incubated at 18° C. during 16 hours. The germinated sporangia were counted under the microscope.

3.2. Inhibition of Blue Mold on Excised Leaves of Tobacco

Leaves from plants (2-leaf stage) were excised from Ky 14 tobacco plants. The petioles of the leaves were placed into 15 ml of a solution of 1% ethanol in water or 15 ml of a solution of 3-n-butyroyloxy-$\beta$-ionone (or another derivative) in 1% ethanol for 1 hour under cool white fluorescent light (ca. 100 E/sec/cm$^2$) in a growth chamber at 20° C. Each leaf was then inoculated with 6 ca. 5-$\mu$l drops of a sporangial suspension of Peronospora tabacina isolate Ky 14 ($10^4$ sporangia/ml). The inoculated leaves were kept in darkness at 100% relative humidity for 24 hours, removed from the solutions, placed on moist filter paper in glass petri dishes for 6–7 days (14 hours light, 100 $\mu$E/sec/cm$^2$, and 10 hour dark in a growth chamber at 20° C. Leaves were then rated for lesion development on a scale of 0–4. After rating, leaves were turned over to their adaxial surface and placed in the dark for 18 hr to permit sporulation.

3.3. Inhibition of Blue Mold on Tobacco Plants

A solution containing 1% ethanol and 0.1% Tween 80 or the solution containing 3-n-butyroyloxy-$\beta$-ionone (or another derivative) was sprayed on the second expanded leaf (ca. 1.5 ml/plant) from the top of Ky 14 tobacco plants in the 3–4 leaf stage. Two hours later, the two leaves above and the leaf below or 5 hours later one leaf above the sprayed leaf were sprayed with a sporangial suspension of isolate Ky 79 of Peronospora tabacina (respectively $1.6\times10^4$ and $1.2\times10^4$ sporangia/ml). Plants were incubated at 20° C. for 6–7 days in growth rooms, rated for disease, placed in plastic bags sprayed internally with water, and incubated for 24 hours at 20° C. in the dark to permit sporulation.

RESULTS

Inhibition of Sporangial Germination

Activity of $\beta$-ionone derivatives as inhibitors of sporangial germination in Peronospora tabacina.

Results of test 3.11.

| Compound | ED$_{50}$(ppm) |
| --- | --- |
| 3(R)-n-butyroyloxy-β-ionone | 0.000006 |
| 3(R)-n-valeroyloxy-β-ionone | 0.000025 |
| Quieson (= 3-isobutyroyloxy-β-ionone) | 0.0003 |

Results of test 3.12.

| Compound | ED$_{50}$(ppm) |
| --- | --- |
| 3(R)-n-butyroyloxy-β-ionone | 0.00000002 |
| 3(R)-pivaloyloxy-β-ionone | 0.000001 |
| 3(R)-methoxyacetoxy-β-ionone | 0.00000008 |
| 3(R)-ethoxyacetoxy-β-ionone | 0.000006 |
| 3(R)-n-hexanoyloxy-β-ionone | 0.00005 |
| Quieson | 0.0004 |

In the following tests 3-acyloxy- -ionone derivatives of the formula I display fungicidal activities.

3.4 Action Against *Phytophthora infestans* on tomato plants (a) Residual-Protective Action Tomato plants are sprayed, after 3-weeks' cultivation, with a spray mixture prepared from the active ingredient formulated as a wettable powder (0.02% of active ingredient). After 24 hours, the treated plants are infested with a suspension of sporangia of the fungus. Evaluation of the fungus attack is made after incubation of the infested plants for 5 days at 20° C. and 90°–100° C. relative humidity.

(b) Systemic Action

A spray mixture prepared from the active ingredient formulated as a wettable powder (0.006% of active ingredient, based on the volume of soil) is applied to tomato plants which have been cultivated for 3 weeks. Care is taken to ensure that the spray mixture does not come in contact with the parts of the plants above the soil. After 48 hours, the treated plants are infested with a suspension of sporangia of the fungus. Evaluation of fungus attack is made after incubation of the infested plants for 5 days at 20° C. and 90–100% relative humidity.

(c) Residual Curative Action

After a cultivation period of three weeks, tomato plants are infested with a suspension of sporangia of the fungus. After an incubation time of 22 hours in a humid chamber at 20° C. and 90–100% relative humidity, the infested plants are dried, and subsequently sprayed with a spray mixture prepared from the active ingredient formulated as wettable powder (0.02% of active ingredient). After the coating has dried, the treated plants are returned to the humid chamber. Evaluation of fungus attack is made 5 days after infestation.

3.5 Action on *Phythium debaryanum* on Sugar Beets (a) Action After Soil Application The fungus is cultivated on carrot chips nutrient solution and added to a mixture of earth and sand. Flower pots are filled with the infected soil, in which sugar beet seeds are then sown. Immediately after sowing, the test preparations are formulated as wettable powders are poured in the form of aqueous suspensions over the soil (20 ppm of active ingredient, based on the volume of the soil). The pots are then stood for 2–3 weeks in a greenhouse at 20°–24° C.. The soil is kept uniformly moist by gently spraying it with water. The emergence of the sugar beet plants as well as the number of healthy and sick plants are ascertained in evaluation of the test.

(b) Action After Seed Dressing Application

The fungus is cultivated on carrot chip nutrient solution and added to a mixture of earth and sand. Flower pots are filled with the infected soil and sugar beet seeds which have been treated with the test preparations formulated as seed dressing powders are sown therein (0.06% of one of the compounds of Table 1). The pots are then stood in a greenhouse for 2–3 weeks at ca. 20° C. The soil is kept uniformly moist by gently spraying it with water. The emergence of the sugar beet plants is ascertained in evaluating the test.

3.6 Action Against *Plasmopara viticola* on Vines Residual Protective Action Vine seedlings in the 4–5 leaf stage are sprayed with a spray mixture (0.006% a.i.) prepared from a wettable powder formulation of the test compound. After 24 hours the treated plants are infected with a sporangia suspension of the fungus. Fungus attack is evaluated after incubation for 6 days at 95–100% relative humidity and 20° C.

We claim:

1. A 3-acyloxy-β-ionone derivative of the formula I

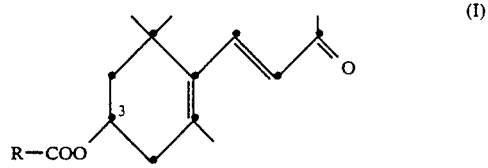

wherein R represents C$_4$–C$_5$alkyl C$_1$–C$_4$alkoxymethyl.

2. A 3(R)-acyloxy-β-ionone derivative of the formula I

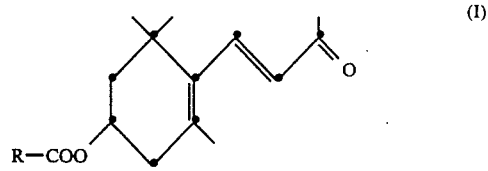

wherein R represents C$_4$–C$_5$ alkyl.

3. 3(R)-n-butyroyloxy-β-ionone according to claim 2.

4. 3-methoxyacetoxy-β-ionone according to claim 1.

5. 3-ethoxyacetoxy-β-ionone according to claim 1.

6. 3-isopropoxyacetoxy-β-ionone according to claim 1.

7. A microbicidal composition for the control of plant-pathogenic comprising as active ingredient an effective amount of 3(R)-acyloxy-β-ionone of the formula I

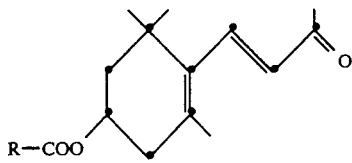
wherein R represents $C_4$–$C_5$ alkyl, together with a suitable carrier.
8. A method of controlling plant-pathogenic microorganisms comprising applying to them a microbicidally effective amount of 3(R)acyloxy-$\beta$-ionone of the formula I
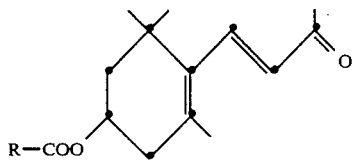
wherein R represents $C_4$–$C_5$ alkyl.
* * * * *